US 011826227B2

(12) United States Patent
Anderson et al.

(10) Patent No.: US 11,826,227 B2
(45) Date of Patent: Nov. 28, 2023

(54) PROSTHETIC VALVE DELIVERY SYSTEM AND METHOD

(71) Applicant: Medtronic Vascular, Inc., Santa Rosa, CA (US)

(72) Inventors: Marc Anderson, Galway (IE); Niall Crosbie, Galway (IE); James R. Keogh, Maplewood, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 487 days.

(21) Appl. No.: 16/950,215

(22) Filed: Nov. 17, 2020

(65) Prior Publication Data

US 2021/0068954 A1     Mar. 11, 2021

Related U.S. Application Data

(62) Division of application No. 15/589,183, filed on May 8, 2017, now Pat. No. 10,856,980.

(51) Int. Cl.
*A61F 2/24* (2006.01)

(52) U.S. Cl.
CPC .......... *A61F 2/2436* (2013.01); *A61F 2/2439* (2013.01)

(58) Field of Classification Search
CPC ........ A61F 2/2436; A61F 2/2439; A61F 2/95; A61F 2/962; A61F 2/966; A61F 2002/9505; A61F 2002/9511
See application file for complete search history.

(56) References Cited

U.S. PATENT DOCUMENTS

| | | | |
|---|---|---|---|
| 5,824,041 A | | 10/1998 | Lenker et al. |
| 6,161,399 A | * | 12/2000 | Jayaraman ............... D04C 1/06 66/170 |
| 6,302,891 B1 | * | 10/2001 | Nadal ....................... A61F 2/95 623/1.11 |
| 10,856,980 B2 | | 12/2020 | Anderson et al. |
| 2002/0029076 A1 | * | 3/2002 | Yee ........................ A61F 2/966 606/108 |
| 2002/0151953 A1 | | 10/2002 | Chobotov et al. |

(Continued)

FOREIGN PATENT DOCUMENTS

| | | |
|---|---|---|
| CN | 101641061 | 2/2010 |
| CN | 102665612 | 9/2012 |

(Continued)

OTHER PUBLICATIONS

International Search Report and Written Opinion for International Application No. PCT/US2018/027860 dated Jul. 20, 2018 (15 pages).

*Primary Examiner* — Darwin P Erezo
*Assistant Examiner* — Christian D Knauss
(74) *Attorney, Agent, or Firm* — Medler Ferro Woodhouse & Mills PLLC (57) ABSTRACT

A valve delivery system and valve delivery method are disclosed. The valve delivery system includes an inner shaft extending along a longitudinal axis and an elongated tension member to continuously circumferentially coil around a prosthetic valve disposed on the inner shaft to form a sheath portion to releasably contain the prosthetic valve on the inner shaft in a compressed state, the elongated tension member extending from the sheath portion along the longitudinal axis of the inner shaft.

14 Claims, 9 Drawing Sheets

(56) References Cited

U.S. PATENT DOCUMENTS

| | | | |
|---|---|---|---|
| 2003/0050684 A1* | 3/2003 | Abrams | G06Q 10/00 623/1.11 |
| 2004/0181272 A1 | 9/2004 | Chambers | |
| 2005/0096721 A1 | 5/2005 | Mangin et al. | |
| 2005/0101968 A1 | 5/2005 | Dadourian | |
| 2005/0154443 A1 | 7/2005 | Linder et al. | |
| 2007/0016281 A1* | 1/2007 | Melsheimer | A61F 2/95 623/1.11 |
| 2007/0239254 A1 | 10/2007 | Chia et al. | |
| 2010/0286768 A1 | 11/2010 | Alkhatib | |
| 2010/0331948 A1 | 12/2010 | Turovskiy et al. | |
| 2011/0040366 A1* | 2/2011 | Goetz | A61F 2/91 623/1.15 |
| 2012/0101562 A1 | 4/2012 | Gunderson et al. | |
| 2012/0277734 A1 | 11/2012 | Goetz et al. | |
| 2013/0096664 A1 | 4/2013 | Goetz et al. | |
| 2013/0096670 A1 | 4/2013 | Goetz et al. | |
| 2013/0103131 A1 | 4/2013 | Goetz et al. | |
| 2013/0245752 A1 | 9/2013 | Goetz et al. | |
| 2013/0325101 A1 | 12/2013 | Goetz et al. | |
| 2013/0338755 A1 | 12/2013 | Goetz et al. | |
| 2014/0330368 A1 | 11/2014 | Gloss et al. | |
| 2015/0112430 A1 | 4/2015 | Creaven et al. | |
| 2017/0128243 A1 | 5/2017 | Shahriari et al. | |
| 2017/0266003 A1 | 9/2017 | Hammer et al. | |
| 2017/0290692 A1 | 10/2017 | Toner et al. | |

FOREIGN PATENT DOCUMENTS

| | | |
|---|---|---|
| CN | 103491903 | 1/2014 |
| CN | 106170269 | 11/2016 |
| WO | 2017083261 A1 | 5/2017 |

\* cited by examiner

PROSTHETIC VALVE DELIVERY SYSTEM AND METHOD

CROSS-REFERENCE TO RELATED APPLICATIONS

This application is a Divisional of U.S. application Ser. No. 15/589,183, filed May 8, 2017, entitled, "PROSTHETIC VALVE DELIVERY SYSTEM AND METHOD," now allowed, the entire teachings of which are incorporated herein by reference.

BACKGROUND

The present disclosure relates to systems and methods for delivering a medical device such as a heart valve. More particularly, it relates to minimally invasive, transcatheter-based systems and methods for delivering a medical device, such as a prosthetic mitral valve.

Many prosthetic valves include stents and stent-grafts that are "self-expanding", i.e., inserted into the vascular system in a compressed or contracted state, and permitted to expand upon removal of a restraint to an expanded or natural state. Self-expanding stents and stent-grafts typically employ a wire or tube configured (e.g., bent or cut) to provide an outward radial force and employ a suitable elastic material such as stainless steel or nitinol (nickel-titanium). Nitinol may additionally employ shape memory properties.

The self-expanding stent, or self-expanding stent-graft, is typically configured in a tubular shape, sized to have a slightly greater diameter than the diameter of the blood vessel in which the stent or stent-graft is intended to be used. In general, rather than inserting it in a traumatic and invasive manner using open surgery, stents and stent-grafts are typically deployed through a less invasive intraluminal delivery, i.e., cutting through the skin to access a lumen or vasculature or percutaneously via successive dilatation, at a convenient (and less traumatic) entry point, and routing the compressed stent or stent-graft in a delivery system through the lumen to the site where the prosthesis is to be deployed.

Intraluminal deployment, in one example, is effected using a delivery catheter with a coaxial inner tube, sometimes called an inner tube, and an outer tube, sometimes called the sheath, arranged for relative axial movement. The prosthetic valve is compressed and typically disposed within the distal end of the sheath in front of the inner tube.

The catheter is then maneuvered, typically routed through a vessel (e.g., lumen), until the end of the catheter containing the prosthetic valve is positioned in the vicinity of the intended treatment site. The inner tube is then held stationary while the sheath of the delivery catheter is withdrawn proximally. The inner tube prevents the prosthetic valve from moving back as the sheath is withdrawn.

As the sheath is withdrawn, the prosthetic valve is gradually exposed from its distal end to its proximal end. The exposed portion of the prosthetic valve radially expands so that at least a portion of the expanded portion is in substantially conforming surface contact with a portion of the interior of the blood vessel wall until it is fully deployed. In order to fully deploy, the sheath must be withdrawn fully from the prosthetic, and in this manner, the deployment site typically requires a length that is equivalent to the length of the prosthetic valve plus the length of the capsule.

In order to deliver the prosthetic valve to the target state, the valve delivery system must often be maneuvered through a tortuous vascular pathway and has limited deployment area. It is desirable to deliver the prosthetic valve with an economical valve delivery system that minimizes the cross-sectional area and length of the delivery system and has a high degree of lateral flexibility to allow passage of through a patient's vascular system.

SUMMARY

One aspect of the present disclosure relates to a valve delivery system including an inner shaft extending along a longitudinal axis and an elongated tension member configured to continuously circumferentially coil around a prosthetic valve disposed on the inner shaft to form a sheath portion to releasably contain the prosthetic valve on the inner shaft in a compressed state. The elongated tension member extends from the sheath portion along the longitudinal axis of the inner shaft.

Another aspect of the present disclosure relates to a valve delivery system including an inner shaft and an elongated tension member. The elongated tension member is extendable along the inner shaft. The elongated tension member is transitional between a first state and a second state. In the first state, a distal portion is continuously coiled successively around a prosthetic valve in a compressed state. The coils of the distal portion extend from a first end to an opposing second end of the prosthetic valve. The prosthetic valve is releasably fixed in the compressed state along the inner shaft in the first state. The distal portion is uncoiled from around the prosthetic valve and the prosthetic valve is expandable from the compressed state in the second state.

Another aspect of the present disclosure relates to a prosthetic valve delivery method. The method includes advancing a valve delivery assembly to a target site through a surgical or vascular pathway of a patient. The valve delivery assembly includes an inner shaft and an elongated tension member including a distal portion continuously circumferentially coiled around a prosthetic valve to releasably fix the prosthetic valve to the inner shaft in a compressed state. A proximal portion of the elongated tension member extends from the distal portion along the inner shaft. The method also includes positioning the prosthetic valve at a target site. The proximal portion of the elongated tension member may extend to outside the patient. The method further includes applying tension to the proximal portion of the elongated tension member, for example, by pulling the elongated tension member proximally, to uncoil the distal portion of the elongated tension member from around the prosthetic valve, releasing the prosthetic valve from the distal portion of the elongated tension member, and expanding the prosthetic valve at the target site.

DETAILED DESCRIPTION

With regard to the terms "distal" and "proximal" within this description, unless otherwise specified, the terms can reference a relative position of the portions of a prosthetic valve and/or an associated valve delivery system with reference to an operator and/or a location in the vasculature or heart. For example, in referring to a valve delivery system suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic valve device, the terms "proximal" and "distal" can refer to the location of portions of the device with respect to the direction of blood flow. For example, proximal can refer to an upstream position or a location where blood flows into the device (e.g., inflow region), and distal can refer to a downstream position or a location where blood flows out of the device (e.g., outflow region).

Embodiments of the present disclosure provide systems, methods and devices to treat heart valves of the body, such as the mitral valve, that address the challenges associated with the anatomy of the mitral valve. The delivery system and methods of the present technology are particularly well-suited for trans-septal approaches, but can also be trans-apical, trans-atrial, and direct aortic delivery of a prosthetic valve to a target location in the heart. Additionally, the embodiments of the systems, devices and methods as described herein can be combined with many known surgeries and procedures, such as known methods of accessing the valves of the heart with antegrade or retrograde approaches, and combinations thereof.

Figure 1:
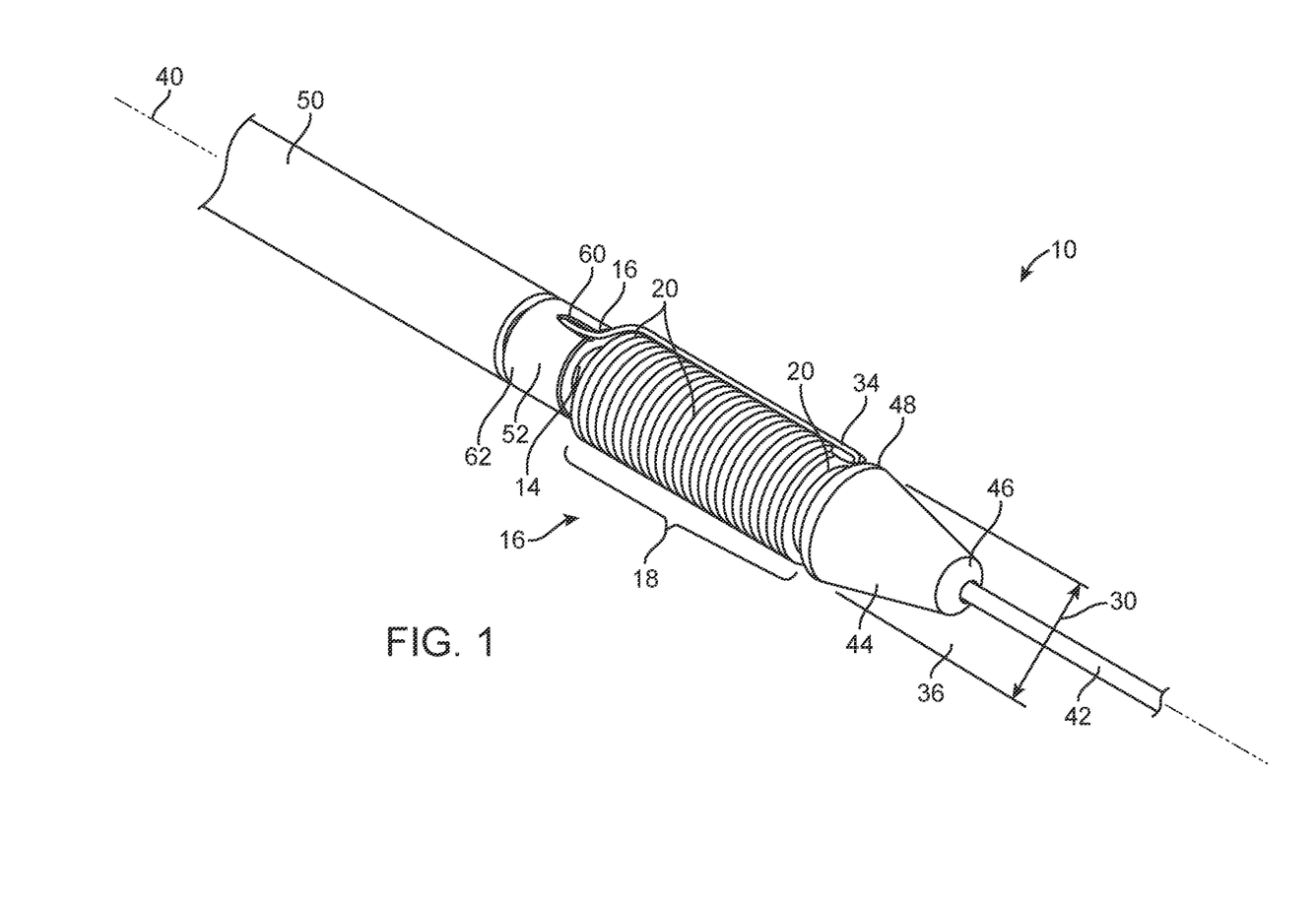
FIG. 1 is a perspective view of a distal portion of a valve delivery system in accordance with aspects of the present disclosure.
Figure 3:
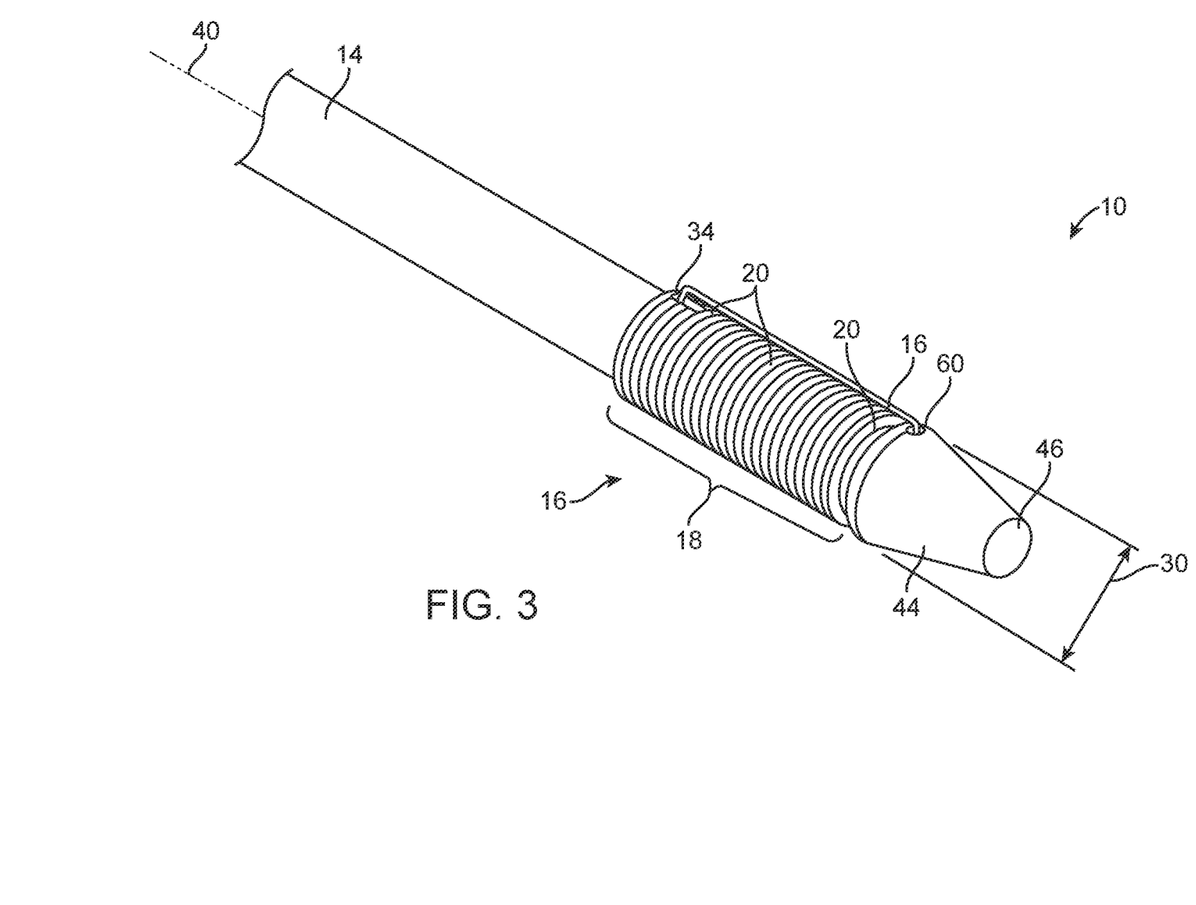
FIG. 3 is a perspective view of a distal portion of a valve delivery system in accordance with aspects of the present disclosure.

FIGS. 1 and 3 are perspective views of a distal portion of valve delivery systems 10 in accordance with aspects of the present disclosure. The valve delivery system 10 provides for delivery of a medical device such as a prosthetic valve 12 through tortuous anatomy and in areas such as cardiac valves. The valve delivery system 10 is not limited to delivering prosthetic valves 12 and can also be employed to deliver other medical devices where it may be useful. The valve delivery system 10 includes an inner shaft 14 and an elongated tension member 16. The prosthetic valve 12 is releasably disposed around the inner shaft 14. The elongated tension member 16 is coiled around the prosthetic valve 12 to releasably maintain the prosthetic valve 12 coupled to the inner shaft 14 in a compressed state, as described in more detail below.

Figure 2:
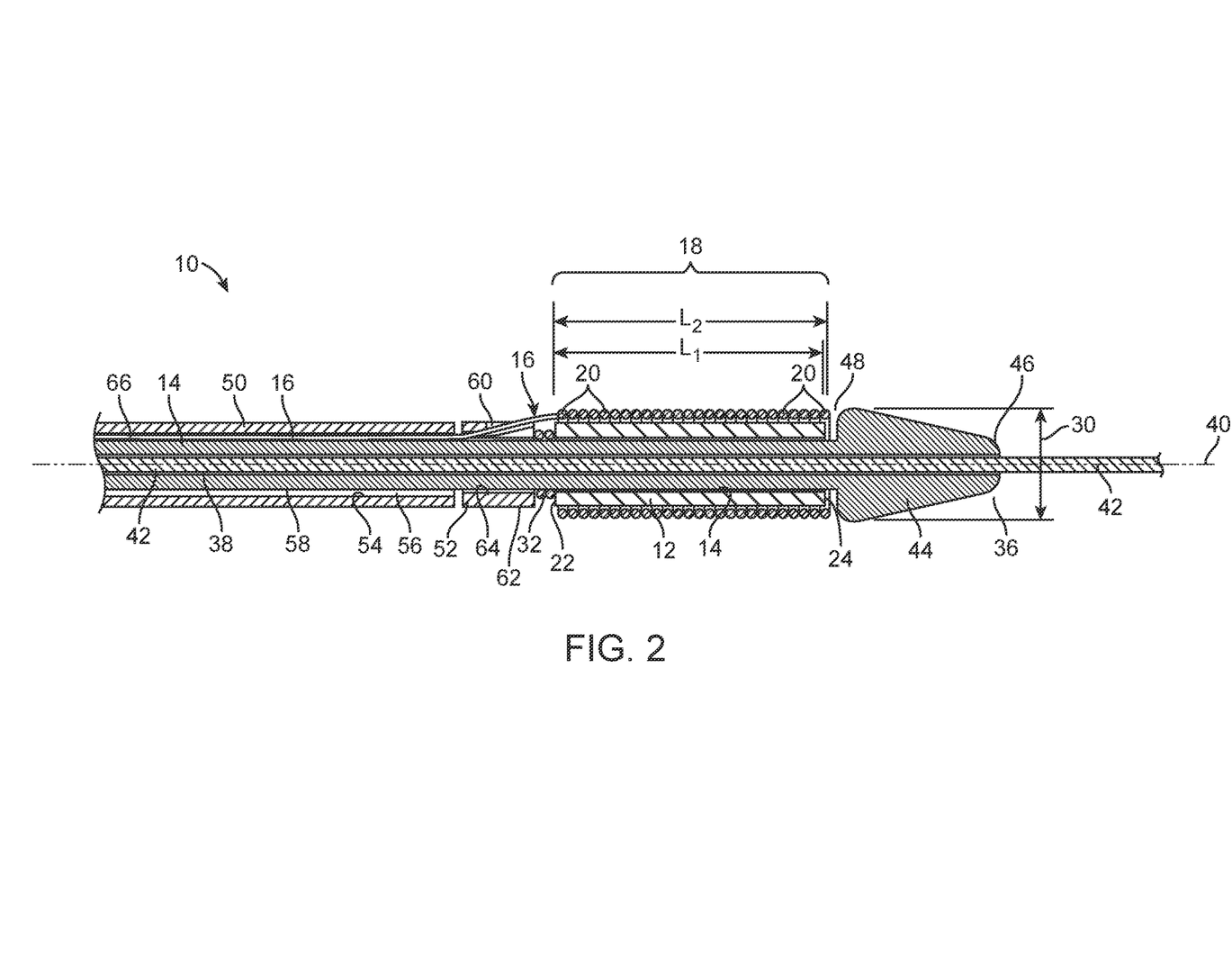
FIG. 2 is a cross-sectional view of the distal portion of the valve delivery system of FIG. 1 in accordance with aspects of the present disclosure.
Figure 4:
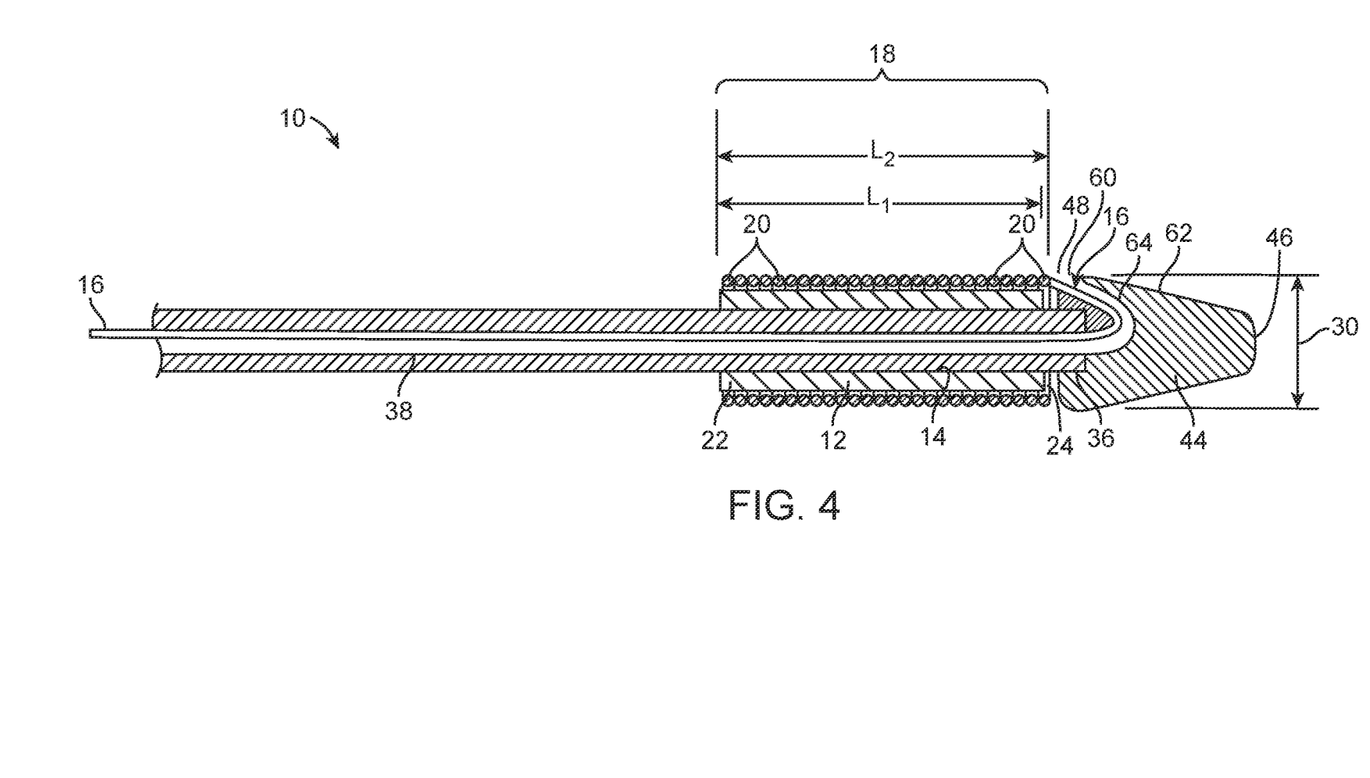
FIG. 4 is a cross-sectional view of the distal portion of the valve delivery system of FIG. 3 in accordance with aspects of the present disclosure.

With additional reference to FIGS. 2 and 4, the elongated tension member 16 in a first state is continuously and successively spiral wound, or coiled, circumferentially around the prosthetic valve 12 to form a sheath, or coiled distal portion, 18 over the prosthetic valve 12 to releasably maintain the prosthetic valve 12 in the compressed state. The quantity of coils 20 is suitable to releasably contain the prosthetic valve 12 in the compressed state during delivery to the target delivery site. For example, a prosthetic valve having a long frame may be compressively retained on the inner member 14 with a longer coiled distal portion 18 than employed for a prosthetic valve having a short frame.

In some embodiments, the coils 20 of the elongated tension member 16 are disposed immediately adjacent to one another and are each in contact alongside adjacently disposed coils 20 of the elongated tension member 16 to form the sheath 18 over the prosthetic valve 12. The coiled distal portion 18 of the elongated tension member 16 in the first state has a longitudinal length $L_1$ along the inner shaft 14 that is substantially equivalent to a length $L_2$ of the prosthetic valve 12 in the compressed state. A bend point is defined along the prosthetic valve 12 between each coil 20 of the elongated tension member 16 providing a flexible coiled sheath 18, or delivery capsule. Adjacently disposed coils 20 of the elongated tension member 16 can completely encase the prosthetic valve 12 from a first end 22 to a second end 24 of the prosthetic valve 12 and effectively form the coiled delivery sheath 18 over the prosthetic valve 12 and ease movement of the prosthetic valve 12 within the patient's vascular system to the target delivery site. In another embodiment, instead of being adjacently disposed, the coils 20 may be separated by varied or constant spaces along the length $L_2$ of the prosthetic valve 12. For example, the coils 20 can be closer together at the first and second ends 22, 24 of the prosthetic valve 12 than around the remainder of the prosthetic valve 12.

The elongated tension member 16 is a generally cylindrical body having a cross-sectional diameter. A small diameter, for example 14-16 French (FR), of the elongated tension member 16 can decrease the overall outside diameter of the delivery system 10 and can increase the quantity of the coils 20 along the length of the prosthetic valve 12 in comparison to a larger diameter, for example 20-22 FR, of the elongated tension member 16. Factors in determining the diameter of the elongated tension member 16 employed can include ease of use, strength, and impact of resulting overall outer diameter of the delivery system 10. An outer diameter 30 of the delivery system 10 can be defined by the outside diameter of the prosthetic valve 12 compressed onto the inner shaft 14 plus two times the diameter of the elongated tension member 16. In one embodiment, the outer diameter 30 of the valve delivery system 10 at the coiled portion 18 around the prosthetic valve 12 is 4.85 mm. A desired outer diameter 30 and flexibility of the valve delivery system 10 can be factors in selecting spacing of the coils 20 and the diameter of the elongated tension member 16. In one embodiment, the flexibility of the valve delivery system 10 along the length $L_2$ of the compressed prosthetic valve 12 can be equivalent to the flexibility of the compressed prosthetic valve 12 alone as the coils 20 of the elongated tension member 16 do not have negative effect on the flexibility of the valve delivery system 10.

The elongated tension member 16 can be any flexible biocompatible member with sufficient tension strength properties to releasably contain the prosthetic valve 12 in a compressed state. In some embodiments, it can be desirable for the elongate tension member 16 to have a low coefficient of friction. In some embodiments, the elongated tension member 16 is a suturing material. The elongated tension member 16 can be absorbable or nonabsorbable, natural or synthetic, braided or monofilament. Synthetic braided materials can include polyglycolic acid, or polyglactin, for example. Monofilamentous forms can include polydioxanone, polytrimethylene carbonate, poliglecaprone, or synthetic polyester. Nonabsorbable material can include surgical steel, silk, cotton, linen, nylon, polypropylene, polyester, or braided nylon/polyester.

In one embodiment, as shown in FIGS. 1 and 2, a first end 32 of the elongated tension member 16 can be securely attached to the inner shaft 14 adjacent to the first end 22 of the prosthetic valve 12. Some non-limited examples of the elongated tension member 16 attachment to the inner shaft 14 include adhesive bonding, over-molding, knot-tying, or laser welding. In one embodiment, the elongate tension member 16 is coiled around the inner shaft 14 at an attachment location proximal to the prosthetic valve 12 and can continue to be coiled along the prosthetic valve 12 from the first end 22 to the second end 24 of the prosthetic valve 12. At the second end 24 of the prosthetic valve 12, the releasable securement and termination of the coiled portion 18 includes a releasable coupling 34 of the elongated tension member 16 such as a looped slip knot through one or more coils or through the second end 24 of the prosthetic valve 12. Other suitable release couplings 34 are also acceptable. Regardless, the releasable coupling 34 is releasable using positive pressure to a proximal length of the elongated tension member 16 extended from the coiled portion 18 when it is desired to unwind the coiled portion 18 and release the prosthetic valve 12.

The inner shaft 14 is tubular and includes a proximal end (not shown), a distal end 36, and a lumen 38 extending along a longitudinal axis 40 between the proximal end and the distal end 36. The lumen 38 is sized to accommodate a guidewire 42 slidably extending within. In some embodiments, the lumen 38 is sized to accommodate the guidewire 42 and a proximal portion 66 of the elongated tension member 16. The proximal portion 66 can extend along the lumen 38 of inner shaft 14, either interior or exterior of the lumen 38. An introducer tip 44, or insertion tip, can be included at the distal end 36 of the inner shaft 14. The introducer tip 44 can be generally conical with rounded edges on both a distal tip 46 and a proximal base 48. The rounded distal tip 46 can ease insertion of the inner shaft 14 into the patient's vascular system for delivery of the prosthetic valve and the rounded edges of the proximal base 48 can ease withdrawal of the inner shaft 14 from the patient's vascular system after the prosthetic valve 12 has been deployed. The proximal base 48 can have a diameter that is at least equal to the outer diameter of the prosthetic valve 12 mounted around the inner shaft 14 in a compressed state and can be substantially equivalent to the outer diameter of the prosthetic valve 12 encompassed by the coiled elongated tension member 16. The proximal base 48 is sized to aid in smooth insertion of the coil encased prosthetic valve 12 and small enough to be minimally invasive.

The valve delivery system 10 can include an outer shaft 50 and a collar 52. The outer shaft 50 and the collar 52 are both tubular and are independently disposed around, and axially moveable relative to, the inner shaft 14. Either, or both, the collar 52 and the outer shaft 50 can be coaxially disposed around the inner shaft 14. The outer shaft 50 is an elongated tubular body having an inner diameter defining an inner surface 54 to accommodate independent axial movement of the inner shaft 14 and the elongated tension member 16. The elongated tension member 16 is extendable within a passageway 56 formed between an outer surface 58 defined by the outer diameter of the inner shaft 14 and the inner surface 54 of the outer shaft 50.

The collar 52 is rotatably disposed around the inner shaft 14. In one embodiment, the collar 52 includes a port 60. The collar 52 is sized and shaped to aid transition of the elongated tension member 16 from the coiled portion 18 around the prosthetic valve 12 into the passageway of the outer shaft 50. The port 60 can be formed as a slotted opening extending from an exterior surface 62 of the collar 52 to an interior surface 64. The port is sized and shaped to allow slidable passage of the elongated tension member 16.

The collar 52 extends longitudinally between the outer shaft 50 and the distal end 36 of the inner shaft 14. The prosthetic valve 12 is releasably disposable around the inner shaft 14 between the introducer tip 44 at the distal end 36 of the inner shaft 14 and the collar 52. The collar 52 and the outer shaft 50 may abut one another and the collar 52 may abut the prosthetic valve 12. The collar 52 and the outer shaft 50 do not axially overlap the prosthetic valve 12. The inner diameter of the outer shaft 50 is less than an outer diameter of the prosthetic valve 12 in the compressed state. In one embodiment, the collar 52 and the outer shaft 50 have substantially equivalent outer diameters.

In one embodiment, as shown in FIGS. 3 and 4, the inner shaft 14 is tubular and includes a proximal end (not shown), a distal end 36, and a lumen 38 extending along a longitudinal axis 40 between the proximal end and the distal end 36. The lumen 38 is sized to accommodate elongated tension member 16 slidably extending within. A valve delivery system tip 44 can be rotatably coupled or disposed around the distal end 36 of the inner shaft 14. The tip 44 can be generally conical with rounded edges on both a distal end 46 and a proximal base 48. The rounded distal tip 46 can ease insertion of the inner shaft 14 into the patient's vascular system for delivery of the prosthetic valve and the rounded edges of the proximal base 48 can ease withdrawal of the inner shaft 14 from the patient's vascular system after the prosthetic valve 12 has been deployed. The proximal base 48 can have a diameter that is at least equal to the outer diameter of the prosthetic valve 12 mounted around the inner shaft 14 in a compressed state and can be substantially equivalent to the outer diameter of the prosthetic valve 12 encompassed by the coiled elongated tension member 16. The proximal base 48 is sized to aid in smooth insertion of the coil encased prosthetic valve 12 and small enough to be minimally invasive.

In one embodiment, the valve delivery system tip 44 includes a port 60. The tip 44 is sized and shaped to aid transition of the elongated tension member 16 from the coiled portion 18 around the prosthetic valve 12 into the lumen 38 of the inner shaft 14. The port 60 can be formed as an opening extending from an exterior surface 62 of the tip 44 to an interior surface 64. The port is sized and shaped to allow slidable passage of the elongated tension member 16.

The prosthetic valve 12 is releasably disposable around the inner shaft 14 proximal the tip 44. A first end of the elongated tension member 16 can be securely attached to the inner shaft 14 adjacent to second end 24 of the prosthetic valve 12. Some non-limited examples of the elongated tension member 16 attachment to the inner shaft 14 include adhesive bonding, over-molding, knot-tying, or laser welding. In one embodiment, the elongate tension member 16 is coiled around the inner shaft 14 at an attachment location distal to the prosthetic valve 12 and can continue to be coiled along the prosthetic valve 12 from the second end 24 to the first end 22 of the prosthetic valve 12. At the first end 22 of the prosthetic valve 12, the releasable securement and termination of the coiled portion 18 includes a releasable coupling 34 of the elongated tension member 16 such as a looped slip knot through one or more coils or through the first end 22 of the prosthetic valve 12. Other suitable release couplings 34 are also acceptable. Regardless, the releasable coupling 34 is releasable using positive pressure to a proximal length of the elongated tension member 16 extended from the coiled portion 18 when it is desired to unwind the coiled portion 18 and release the prosthetic valve 12.

The valve delivery system 10 is comprised of biocompatible materials. For example, the inner and outer shafts 14, 50 can be polytetrafluoroethylene (PTFE), polyethylene, polyethylene terephthalate (PET), or polyurethane. In one embodiment, the outer shaft 50 is formed of polyurethane and the inner shaft 14 is formed of PTFE. In another embodiment, the outer shaft 50 is a polyamide such as a nylon or a polyamide derivative (e.g., Pebax®). In one embodiment, the prosthetic valve 12 is assembled to the inner shaft 14 of the valve delivery system 10 and the elongated tension member 16 manually coiled around the prosthetic valve 12. In another embodiment, the elongated tension member 16 is mechanically coiled around the prosthetic valve 12 with a coiling device. The prosthetic valve 12 can be assembled to the valve delivery system 10 either at a medical facility, such as a hospital, or pre-assembled prior to delivery to the medical facility.

In one embodiment, the prosthetic valve 12 is crimped from an expanded state to a compressed state onto the inner shaft 14 with the elongated tension member 16 as the elongated tension member 16 is coiled around the prosthetic valve 12 with applied circumferential tension to both the prosthetic valve 12 and the elongated tension member 16. A compressing assembly device, such as a funnel, for example, can be used to at least partially compress the prosthetic valve 12 prior to and/or during coiling the elongated tension member 16 around the prosthetic valve 12, using the elongated tensioning member 16 to more fully and completely compress the prosthetic valve 12 to the compressed state. Other methods of compressing the prosthetic valve 12 prior to, or during, coiling the elongated tension member 16 around the prosthetic valve 12 are also acceptable. In one embodiment, the collar 52 and the outer shaft 50 can be slidably assembled over the inner shaft 14 subsequent to the elongated tension member 16 coiling. A proximal portion 66 of the elongated tension member 16 is extended from the distal coiled portion 18 and through the port 60 of the collar 52 and within the passageway 56 formed between the outer shaft 50 and the inner shaft 14 to terminate outside a proximal end (see, e.g., FIG. 5A) of the outer shaft 50.

Depending on the point of vascular access, access to the mitral valve may be antegrade and may rely on entry into the left atrium by crossing the inter-atrial septum (e.g., a trans-septal approach). Alternatively, access to the mitral valve can be retrograde where the left ventricle is entered through the aortic valve. Access to the mitral valve may also be achieved using a trans-apical approach. Depending on the approach, the interventional tools and supporting catheter(s) may be advanced to the heart intravascularly and positioned adjacent the target cardiac valve in a variety of manners, as described herein.

Figure 5A:
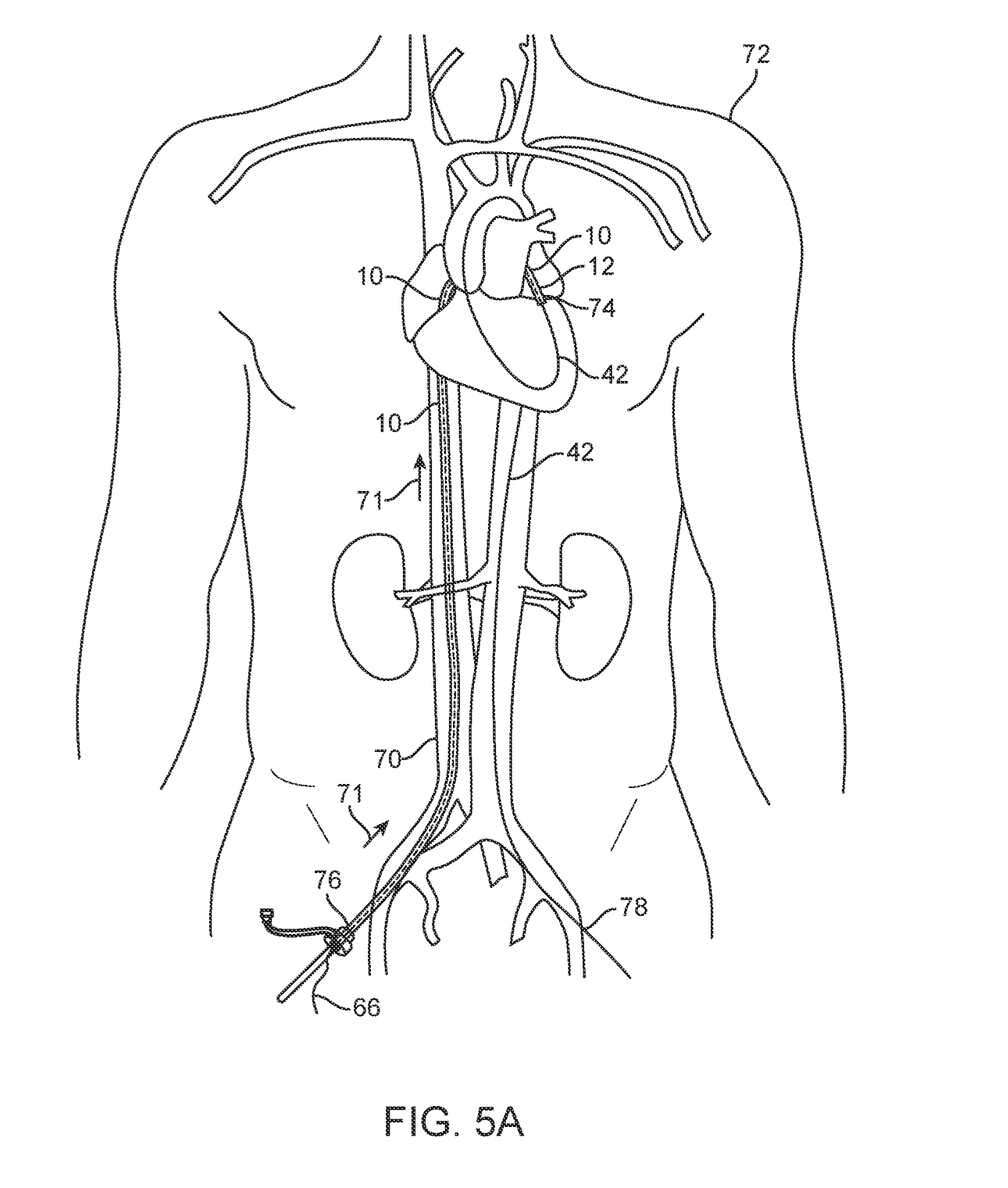
FIG. 5A is a schematic view of a valve delivery system and valve delivery pathway of a patient in accordance with aspects of the present disclosure.
Figure 5B:
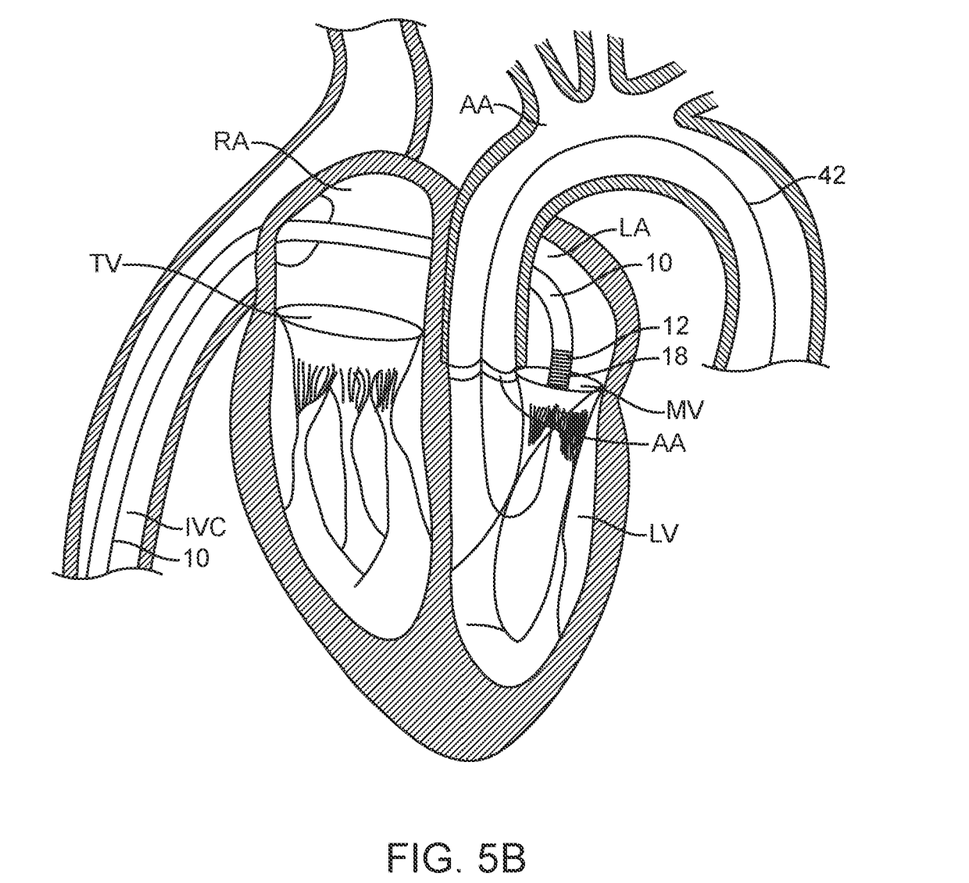
FIG. 5B is a schematic cross-sectional view of a heart showing an antegrade trans-septal approach to the mitral valve from the venous vasculature in accordance with aspects of the present disclosure.

FIGS. 5A and 5B schematically illustrate the valve delivery system 10 as the valve delivery system 10 is advanced through a vascular pathway 70 of a patient 72 and the prosthetic valve 12 carried on the valve delivery system 10 is positioned at a target site 74 (e.g., a mitral valve). As illustrated in FIGS. 5A and 5B, the valve delivery system 10 can be inserted at a venous access site 76 (e.g., a femoral vein) and advanced through the vascular pathway 70 in an antegrade direction indicated by arrow 71 over the guidewire 42, such as a flossing guidewire that enters a femoral vein, passes though the inferior vena cava IVC to the right atrium RA, crosses the septum to the left atrium LA, passes through the mitral valve MV to the left ventricle LV, passes through the aortic valve AV to the aorta arch AA, and exits a left femoral artery. In one embodiment, once the prosthetic valve 12 is positioned at the target site 74, as illustrated in FIGS. 5A and 5B, tension can be applied to the proximal portion 66 of the elongated tension member 16 extended outside the vascular pathway 70, causing the distal coiled portion 18 of the elongated tension member 16 to begin uncoiling from and releasing the prosthetic valve 12. Tension can be manually applied or applied using an actuator, for example.

With additional reference to FIGS. 1 and 2, the collar 52 can rotate around the inner shaft 14 as coiled portion 18 of the elongated tension member 16 is removed from the prosthetic valve 12 and withdrawn through the passageway 56 in the direction indicated by arrow 75 within the outer shaft 50. The uncoiling of the elongated tension member 16 and release of the prosthetic valve 12 begins at the second end 24 of the prosthetic valve 12 and proceeds with the uncoiling of each coil 20 sequentially until the coiled portion 18 of the elongated tension member 16 is removed from the first end 22 of the prosthetic valve 12. The prosthetic valve 12 can be self-expanding and the uncoiling of the elongated tension member 16 can occur one coil at a time starting at the second end 24 and continuing to the first end 22 for release and full deployment of the prosthetic valve 12. With the distal portion of the elongated tension member 16 being withdrawn proximally through the outer shaft 50 while being uncoiled, a deployment length of the valve delivery system 10 does not need to be greater than the length of the prosthetic valve 12. The speed of the uncoiling and release of the prosthetic valve 12 can be continuously controlled by the adjusting or maintaining the amount of tension applied to the proximal portion 66 of the elongated tension member 16. After removal of the coiled portion 18 from the prosthetic valve 12, the distal end of the elongated tension member 16 can be maintained by the inner shaft 14 or the collar for concurrent withdrawal with the inner and outer shafts 14, 50 from the patient. Although a venous access site 76 is illustrated in FIG. 5A, it is understood that a femoral access site 78 at the opposite end of the flossing guidewire 42 can be used for insertion of the valve delivery system 10.

Figure 6:
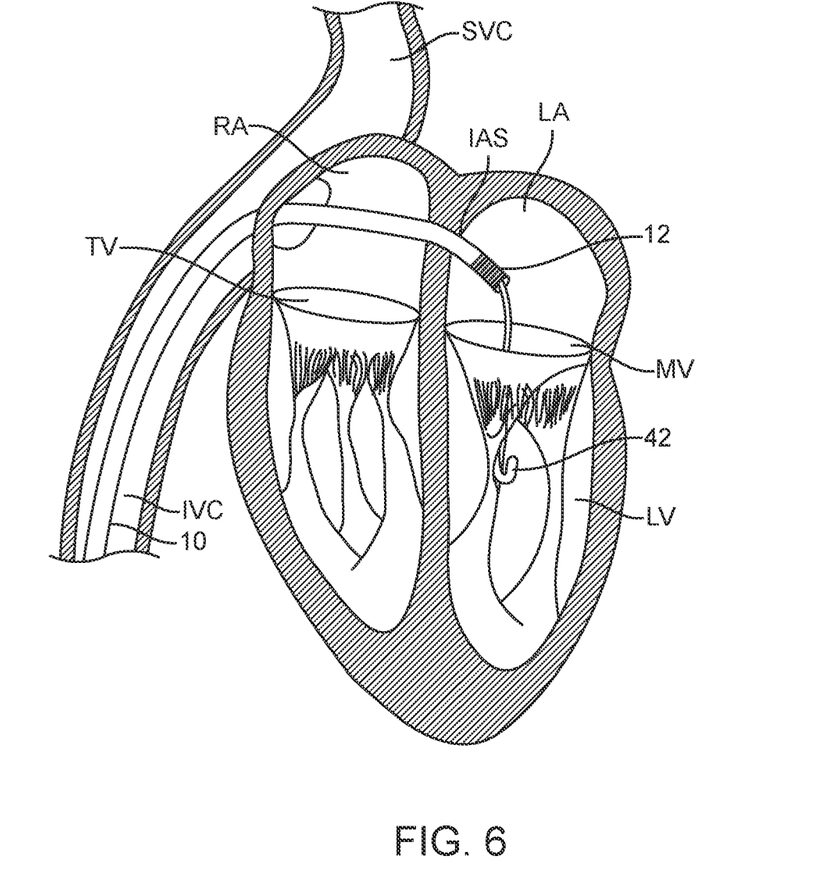
FIG. 6 is a schematic cross-sectional view of a heart showing an antegrade trans-septal approach to the mitral valve from the venous vasculature in accordance with aspects of the present disclosure.

FIG. 6 illustrates a trans-septal approach for implanting the prosthetic valve 12 carried on the valve delivery system 10 at a mitral valve MV. In a trans-septal approach, access is via the inferior vena cava IVC or superior vena cava SVC, through the right atrium RA, across the inter-atrial septum IAS, and into the left atrium LA above the mitral valve MV. As shown in FIG. 6, a valve delivery system 10 tracks over a guidewire 42, which previously had its distal end positioned in the left ventricle LV. The valve delivery system 10 moves from the inferior vena cava IVC, through the right atrium RA, through the septal wall, for example at the fossa ovalis or the foramen ovale, and into the left atrium LA. The guidewire 42 provides access to the mitral valve for implanting a prosthetic valve 12 in accordance with the technology.

Figure 7:
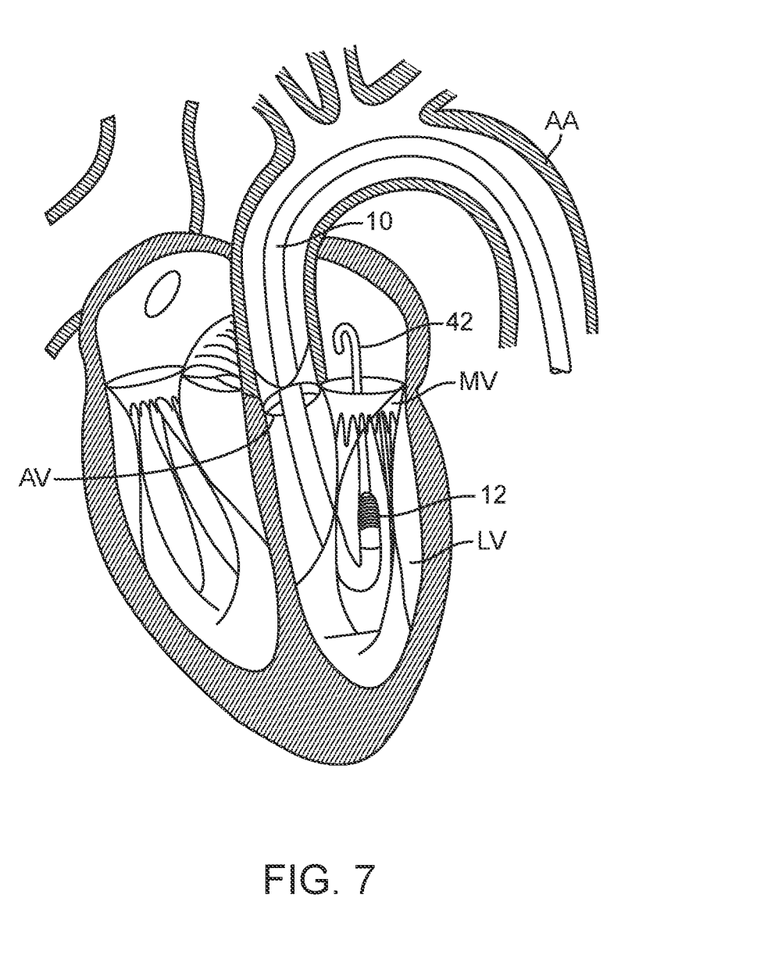
FIG. 7 is a schematic cross-sectional view of a heart showing a retrograde approach to the mitral valve through the aortic valve and arterial vasculature in accordance with aspects of the present disclosure.

FIG. 7 illustrates a retrograde approach for implanting the prosthetic valve 12 carried on the valve delivery system 10 at a mitral valve MV. Access to the mitral valve MV may be achieved from the aortic arch AA, across the aortic valve AV, and into the left ventricle LV below the mitral valve MV. The aortic arch AA may be accessed through a conventional femoral artery access route or through more direct approaches via the brachial artery, axillary artery, radial artery, or carotid artery. Such access may be achieved with the use of a guidewire 42. Retrograde approaches do not need a trans-septal puncture.

Figure 8:
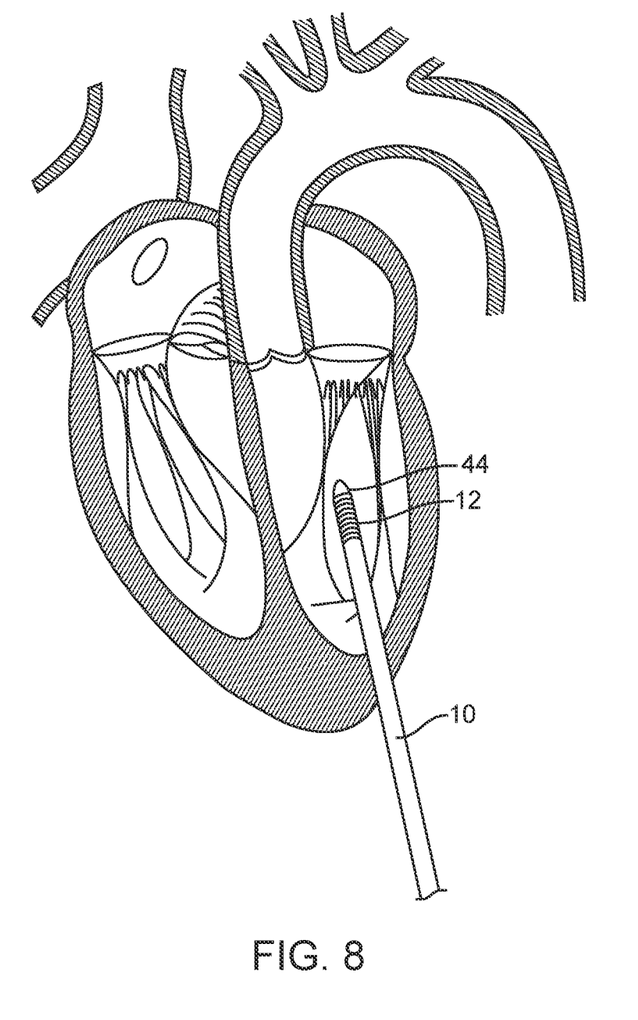
FIG. 8 is a schematic cross-sectional view of a heart showing an approach to the mitral valve using a trans-apical puncture in accordance with aspects of the present disclosure.

FIG. 8 illustrates a transapical approach via a transapical puncture. In this approach, access to the heart is via a thoracic incision, which can be a conventional open thoracotomy or sternotomy, or a smaller intercostal or subxyphoid incision or puncture. Valve delivery system 10 is then placed through a puncture in the wall of the left ventricle at or near the apex of the heart. The transapical approach provides a shorter, straighter, and more direct path to the mitral or aortic valve. In one embodiment, once the prosthetic valve 12 is positioned at the mitral valve tension can be applied to the proximal portion 66 of the elongated tension member 16 causing the distal coiled portion 18 of the elongated tension member 16 to begin uncoiling from and releasing the prosthetic valve 12. Tension can be manually applied or applied using an actuator, for example. With additional reference to FIGS. 3 and 4, the tip 44 can rotate around the inner shaft 14 as coiled portion 18 of the elongated tension member 16 is removed from the prosthetic valve 12 and withdrawn in a proximal direction through the lumen 38 of the valve delivery system 10. The uncoiling of the elongated tension member 16 and release of the prosthetic valve 12 begins at the first end 22 of the prosthetic valve 12 and proceeds with the uncoiling of each coil 20 sequentially until the coiled portion 18 of the elongated tension member 16 is removed from the second end 24 of the prosthetic valve 12. The prosthetic valve 12 can be self-expanding and the uncoiling of the elongated tension member 16 can occur one coil at a time starting at the first end 22 and continuing to the second end 24 for release and full deployment of the prosthetic valve 12. With the distal portion of the elongated tension member 16 being withdrawn proximally through lumen 38 while being uncoiled, a deployment length of the valve delivery system 10 does not need to be greater than the length of the prosthetic valve 12. The speed of the uncoiling and release of the prosthetic valve 12 can be continuously controlled by the adjusting or maintaining the amount of tension applied to the proximal portion 66 of the elongated tension member 16.

In view of the above, it is understood that the valve delivery system 10 is not limited to use with a prosthetic valve and that the valve delivery system 10 can also be employed to deliver other structural heart devices including devices used for remodeling the heart chambers or for restoration of the septal wall, including septal sealing, cariogenic shock, heart failure, or any other device delivery that a typical delivery capsule is not desired.

Although the present disclosure has been described with reference to preferred embodiments, workers skilled in the art will recognize that changes can be made in form and detail without departing from the spirit and scope of the present disclosure.

What is claimed is:

1. A valve delivery system, comprising:
    an inner shaft defining a longitudinal axis and a lumen extending along the longitudinal axis;
    a tip coupled to the inner shaft, the tip having a port formed as an opening extending from an exterior surface of the tip to an interior surface of the tip; and
    an elongated tension member routed through the lumen and the port, the elongated tension member being configured to circumferentially coil around a prosthetic valve disposed on the inner shaft to form a sheath portion to at least partially restrain the prosthetic valve on the inner shaft in a compressed state.

2. The valve delivery system of claim 1, wherein the tip is rotatably coupled around a distal end of the inner shaft.

3. The valve delivery system of claim 1, further comprising a releasable coupling that is releasable using positive pressure to a proximal length of the elongated tension member.

4. The valve delivery system of claim 3, wherein the releasable coupling is a looped knot through one or more coils of the elongated tension member.

5. The valve delivery system of claim 1, wherein the port is sized and shaped to allow for slidable passage of the elongated tension member.

6. The valve delivery system of claim 1, wherein when the prosthetic valve is in the compressed state, the elongated tension member extends from the lumen to the opening and out of the tip at the port.

7. The valve delivery system of claim 1, wherein when the prosthetic valve is in the compressed state, one portion of the elongated tension member is coiled around a second portion of the elongated tension member.

8. A valve delivery system, comprising:
    an inner shaft defining a longitudinal axis;
    a tip coupled to the inner shaft, the tip having a port formed as an opening extending from an exterior surface of the tip to an interior surface of the tip; and
    an elongated tension member routed through the port, wherein at least a portion of the elongated tension member slides through the port as the elongated tension member is tensioned, the elongated tension member being configured to circumferentially coil around a prosthetic valve disposed on the inner shaft to form a sheath portion to releasably contain the prosthetic valve on the inner shaft in a compressed state, the elongated tension member extending from the sheath portion along the longitudinal axis of the inner shaft.

9. The valve delivery system of claim 8, wherein the tip is rotatably coupled around a distal end of the inner shaft.

10. The valve delivery system of claim 8, further comprising a releasable coupling that is releasable using positive pressure to a proximal length of the elongated tension member.

11. The valve delivery system of claim 10, wherein the releasable coupling is a looped knot through one or more coils of the elongated tension member.

12. The valve delivery system of claim 8, wherein the inner shaft defines a lumen; wherein when the prosthetic valve is in the compressed state, the elongated tension member extends from the lumen to the opening and out of the tip at the port.

13. The valve delivery system of claim 8, wherein the inner shaft includes a lumen along the longitudinal axis in which the elongated tension member is routed.

14. The valve delivery system of claim 13, wherein when the prosthetic valve is in the compressed state, the elongated tension member is coiled around a portion of the elongated tension member positioned within the lumen.

* * * * *